United States Patent
Yabugami

(10) Patent No.: US 9,724,064 B2
(45) Date of Patent: Aug. 8, 2017

(54) RADIOGRAPHIC APPARATUS

(71) Applicant: SHIMADZU CORPORATION, Kyoto (JP)

(72) Inventor: Katsuhiro Yabugami, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 309 days.

(21) Appl. No.: 14/455,601

(22) Filed: Aug. 8, 2014

(65) Prior Publication Data

US 2014/0348292 A1    Nov. 27, 2014

Related U.S. Application Data

(63) Continuation of application No. PCT/JP2012/000917, filed on Feb. 10, 2012.

(51) Int. Cl.
  *A61B 6/00* (2006.01)
  *A61B 5/107* (2006.01)

(52) U.S. Cl.
  CPC ............ *A61B 6/487* (2013.01); *A61B 5/1075* (2013.01); *A61B 6/488* (2013.01); *A61B 6/544* (2013.01); *A61B 6/545* (2013.01)

(58) Field of Classification Search
  CPC ....... A61B 5/1075; A61B 6/487; A61B 6/488; A61B 6/544; A61B 6/545
  See application file for complete search history.

(56) References Cited

U.S. PATENT DOCUMENTS

2004/0066897 A1    4/2004 Takahashi et al.

FOREIGN PATENT DOCUMENTS

| CN | 1498093 A | 5/2004 |
|---|---|---|
| JP | 09-271023 A | 10/1997 |
| JP | 2000-012280 A | 1/2000 |
| JP | 2000-261724 A | 9/2000 |
| JP | 2001-340321 A | 12/2001 |

OTHER PUBLICATIONS

Translation of CN 1498093, which was published on May 19, 2004.*

(Continued)

*Primary Examiner* — Glen Kao
(74) *Attorney, Agent, or Firm* — McDermott Will & Emery LLP

(57) ABSTRACT

Provided is a radiographic apparatus configured to obtain an animated image of a fluoroscopic image, and thereafter complete fluoroscopy temporarily for taking a static image or the animated image for diagnosis, the radiographic apparatus allowing taking an image of a subject with suitable brightness. The apparatus determines a control condition (radiography condition) of an X-ray tube for taking the static image in accordance with the control condition of the X-ray tube upon obtaining the fluoroscopic image. With the disclosure, brightness of the subject contained in the fluoroscopic image is also regarded upon determination of the radiography condition. This achieves obtaining the suitable radiography condition even when obtaining the animated image stops before radiation has appropriate intensity during obtaining a live image. Accordingly, the apparatus in the disclosure allows obtaining a clear image with appropriate exposure.

5 Claims, 4 Drawing Sheets

(56) References Cited

OTHER PUBLICATIONS

International Search Report and Written Opinion issued in International Application No. PCT/JP2012/000917 mailed Mar. 27, 2012, with partial English translation.
Chinese Office Action issued in Application No. 201280069420.4 dated Nov. 24, 2015, with English translation.
Chinese Office Action issued in Application No. 201280069420.4 dated Sep. 2, 2016, with English translation.

* cited by examiner

| FLUOROSCOPY CONTROL CONDITION | STANDARD BODY THICKNESS |
|---|---|
| CONTROL CONDITION 1 | 10cm |
| CONTROL CONDITION 2 | 15cm |
| CONTROL CONDITION 3 | 20cm |
| CONTROL CONDITION 4 | 25cm |
| | |

| BRIGHTNESS DIFFERENCE | CORRECTION VALUE |
|---|---|
| 10 | 2cm |
| 20 | 3cm |
| −10 | −2cm |
| −20 | −4cm |

| BODY THICKNESS | RADIOGRAPHY CONDITION |
|---|---|
| 10cm | RADIOGRAPHY CONDITION 1 |
| 15cm | RADIOGRAPHY CONDITION 2 |
| 20cm | RADIOGRAPHY CONDITION 3 |
| 25cm | RADIOGRAPHY CONDITION 4 |
| | |

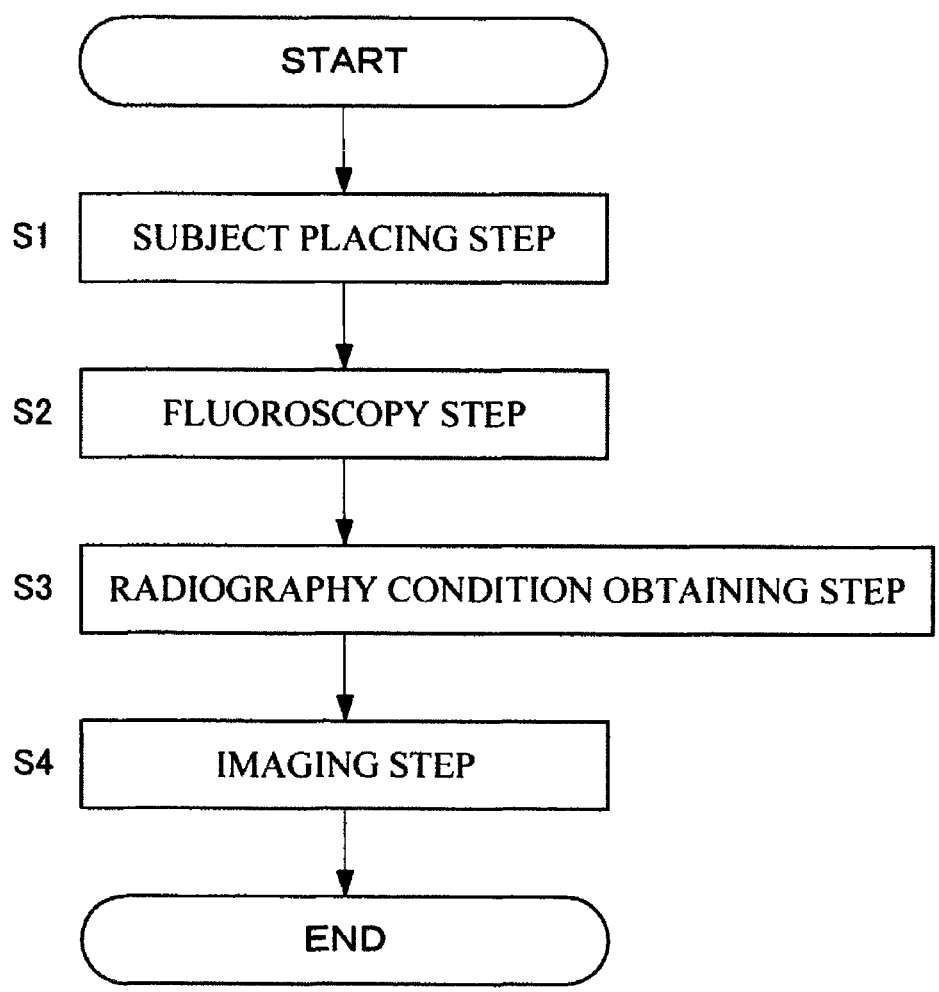

RADIOGRAPHIC APPARATUS

RELATED APPLICATIONS

This application is a continuation of International Application No. PCT/JP2012/000917, filed on Feb. 10, 2012, the disclosure of which Application is incorporated by reference herein.

TECHNICAL FIELD

The present invention relates to a radiographic apparatus configured to perform fluoroscopy to a subject in advance and thereafter take a diagnostic image.

BACKGROUND ART

Medical institutions are equipped with a radiographic apparatus configured to emit radiation to image a subject. Such a radiographic apparatus conducts fluoroscopy to the subject while emitting weak radiation to the subject and thereafter emitting strong radiation to the subject, thereby imaging the subject. See, for example, Japanese Patent Publication No. 2000-261724A and H09-271023A.

In the fluoroscopy of the subject, weak radiation is repeatedly emitted, whereby an animated image (animated image) containing a fluoroscopic image of the subject is obtained. Accurate diagnosis cannot be conducted with the animated image (animated image) obtained in the above manner. An operator controls a position of the subject while observing the animated image such that a region of interest of the subject is located within a field of view of the radiographic apparatus.

Upon completing the control in position of the subject, the operator stops obtaining the animated image. Thereafter, the operator issues a command to the radiographic apparatus to conduct radiography to the subject so as not to move the subject in this condition. Then, the radiographic apparatus irradiates the subject with strong pulsed radiation, thereby taking an image (static image) containing a fluoroscopic image of the subject. The taken image contains a clear fluoroscopic image of the subject. Then, the operator conducts various diagnoses in accordance with the image.

The following describes a conventional method in detail. Upon starting fluoroscopy to a subject, the radiographic apparatus firstly acquires brightness of the fluoroscopic image of the subject appearing in the animated image. Thereafter, the radiographic apparatus performs feedback control to radiation irradiation control such that the brightness becomes appropriate brightness. Consequently, if the animated image contains a dark fluoroscopic image of the subject due to the too thick subject, the fluoroscopy is continuously conducted while intensity of radiation gradually increases with the feedback control.

In this manner, the conventionally apparatus automatically controls the intensity of radiation while the fluoroscopy is continuously conducted. Immediately before completing the fluoroscopy, the animated image contains the fluoroscopic image of the subject with the brightness appropriate to visual recognition. Under this state, the fluoroscopy is completed.

After the fluoroscopy, radiography is performed to the subject. For the radiography, it is necessary to determine a control condition (radiography condition) of a radiation source in advance. This is because a suitable radiography condition varies depending on a frame of the subject, and thus is not uniform.

As a result, the conventionally apparatus determines the radiography condition from a feature that the feedback control is performed to irradiation by the radiation source during the fluoroscopy. That is, the radiography condition is obtained in accordance with radiation intensity immediately before completion of the fluoroscopy. As in the above embodiment, when the subject is too thick, the fluoroscopy is performed with higher intensity of radiation. Then radiography is performed with increased intensity of radiation accordingly, achieving a suitable radiography condition.

In this manner, the conventionally apparatus performs feedback control to the fluoroscopy condition depending on a thickness of the subject, and determines the radiography condition for taking an image in accordance with the controlled fluoroscopy condition. For concrete setting of the radiography condition, a thickness of the subject is estimated in accordance with radiation intensity immediately before completion of the fluoroscopy. Thereafter, radiation intensity upon radiography is set in accordance with the estimated body thickness.

PATENT LITERATURE

Patent Literature 1 Japanese Patent Publication No. 2000-261724A

Patent Literature 2 Japanese Patent Publication 9-271023A

SUMMARY OF INVENTION

Technical Problem

However, the following drawbacks may arise in the conventional radiographic apparatus. Specifically, the conventional radiographic apparatus has a drawback that it is not always possible to take an image with suitable radiation intensity. That is, a radiography condition becomes unsuitable when the fluoroscopy is completed before the radiation intensity during the fluoroscopy becomes appropriate.

In recent years, the radiographic apparatus allows brightness correction through processing to the animated image. Such an apparatus corrects the animated image with increased brightness through the image processing even when the animated image contains the darker fluoroscopic image of the subject. The operator visually recognizes the animated image whose quality is corrected with increased brightness, thereby stopping controlling the position of the subject rapidly and additionally stopping fluoroscopy. This derives from necessity of decreasing exposure to the subject.

That is, the apparatus having an image processing function allows suppression of radiation exposure to the subject by rapid completion of the fluoroscopy. On the other hand, the apparatus completes the fluoroscopy before the fluoroscopy condition is controlled insufficiently. Insufficient control of the fluoroscopy condition causes inappropriate radiation intensity immediately before completion of the fluoroscopy.

The following describes a reason for the above. As one extreme case, the fluoroscopy may be completed while no feedback control is performed to the irradiation condition of the radiation source from a state of starting the fluoroscopy. Accordingly, the radiography condition is to be determined in accordance with the irradiation condition not controlled at all. The obtained radiography condition is an underexposed condition with a large body thickness of the subject, whereas the obtained radiography condition is an overexposed condition with a small body thickness of the subject.

Even when the feedback control is performed to the irradiation condition of the radiation source during fluoroscopy, underexposure or overexposure for radiography may occur if the fluoroscopy is suspended before a suitable irradiation condition is obtained. At this time, the radiography includes fewer defects than that when no feedback control is performed to the irradiation condition of the radiation source. However, the fact still remains that the image has poor visibility.

Accordingly, radiography is performed in a suitable condition when no image processing is performed to the animated image until the animated image has appropriate brightness through the feedback control of the radiation source. On the other hand, this requires some time to obtain the animated image with a stable quality, leading to undesirable exposure to the subject.

The present invention has been made regarding the state of the art noted above, and its one object is to provide a radiographic apparatus configured to perform fluoroscopy to a subject by irradiating a subject with weak radiation and thereafter to perform radiography to the subject by irradiating the subject with strong radiation, the radiographic apparatus allowing obtaining an image of the subject with suitable brightness.

Solution to Problem

The present invention adopts the following construction for overcoming the above drawback. Specifically, one embodiment of the present invention discloses a radiographic apparatus including a radiation source configured to emit radiation, a radiation source controller configured to control the radiation source, a detecting device configured to detect radiation through a subject to output a detection signal, a fluoroscopic-image generating device configured to generate an animated image of a fluoroscopic image of the subject in accordance with the detection signal, a brightness acquiring device configured to acquire brightness of the subject contained in the fluoroscopic image, a radiography condition obtaining device configured to obtain a radiography condition in accordance with the brightness of the subject in the fluoroscopic image and a control condition of the radiation source upon obtaining the fluoroscopic image, the radiography condition corresponding to a control condition of the radiation source upon taking a static image or the animated image subsequent to obtaining the fluoroscopic image, and an image generating device configured to generate the static image or the animated image in accordance with the detection signal, the detection signal being outputted from the detecting device by detecting the radiation emitted from the radiation source in accordance with the radiography condition.

Operation and Effect

The apparatus in the embodiment of the present invention obtains the animated image of the fluoroscopic image, and thereafter completes fluoroscopy temporarily for taking the animated image of the static image for diagnosis. The apparatus in the embodiment of the present invention determines the control condition (radiography condition) of the radiation source for taking the static image or the animated image in accordance with the control condition of the radiation source upon obtaining the fluoroscopic image. On the other hand, the radiography condition is determined under this state regardless of a body thickness of the subject. Consequently, the radiography condition is not always suitable. Accordingly, in the embodiment of the present invention, the brightness of the subject contained in the fluoroscopic image is also regarded upon determination of the radiography condition. Here, the brightness of the subject varies depending on the body thickness of the subject. Consequently, correction of the radiography condition depending on the brightness of the subject achieves a suitable radiography condition depending on the body thickness of the subject. As a result, the embodiment of the present invention allows obtaining the suitable radiography condition even when obtaining the animated image stops before the radiation has appropriate intensity during obtaining the animated image. The apparatus in the embodiment of the present invention allows obtaining a clear static image with appropriate exposure.

Moreover, it is more preferable that the radiation source controller of the radiographic apparatus performs feedback control to the radiation source upon obtaining the fluoroscopic image in accordance with the brightness of the subject in the fluoroscopic image obtained with the brightness acquiring device.

Operation and Effect

The foregoing configuration is a concrete example of the apparatus according to the embodiment of the present invention. When the present invention is applied to a configuration of performing feedback control to the radiation source upon obtaining the fluoroscopic image, a clear radiographic image with appropriate exposure is obtainable even if taking the fluoroscopic image stops before the suitable control condition of the radiation source upon obtaining the fluoroscopic image becomes suitable through the feedback control.

Moreover, it is more preferable that the radiographic apparatus includes an input device configured to input variations in the radiation irradiation condition by an operator upon obtaining the fluoroscopic image.

Operation and Effect

The foregoing configuration is a concrete example of the apparatus according to the embodiment of the present invention. The present invention is applicable to the apparatus that allows variations in the radiation irradiation condition upon obtaining the fluoroscopic image. Although the operator misjudges visually upon changing the radiation irradiation condition to be suitable upon obtaining the fluoroscopic image, the function of the apparatus according to the present invention naturally achieves the suitable radiography condition.

Moreover, it is more preferable that the radiography condition obtaining device of the radiographic apparatus includes a body thickness estimating device configured to estimate a body thickness of the subject in accordance with the control condition of the radiation source upon obtaining the fluoroscopic image and the brightness of the subject in the fluoroscopic image, and a body-thickness correspondence-condition obtaining device configured to obtain a control condition of the radiation source corresponding to the estimated body thickness.

Operation and Effect

The foregoing configuration is a concrete example of the apparatus according to the embodiment of the present invention. In the embodiment of the present invention, the radiography condition is obtained by temporarily estimating the body thickness of the subject. This achieves rapid adaptation to variations in configuration of the apparatus, and additionally ensures to obtain the radiography condition.

Moreover, it is more preferable that the radiographic apparatus preferably includes a storing device configured to store a correspondence between the control condition of the radiation source upon obtaining the fluoroscopic image and the body thickness and a correspondence between the body thickness and the radiography condition.

Operation and Effect

The foregoing configuration is a concrete example of the apparatus according to the embodiment of the present invention. Obtaining the radiography condition in accordance with information stored in the storing device ensures to obtain the radiography condition rapidly.

Advantageous Effects of Invention

The apparatus in the embodiment of the present invention obtains the animated image of the fluoroscopic image, and thereafter completes fluoroscopy temporarily for taking the animated image or the static image for diagnosis. The apparatus in the embodiment of the present invention determines the control condition (radiography condition) of the radiation source for taking the static image or the animated image in accordance with the control condition of the radiation source upon obtaining the fluoroscopic image. With the embodiment of the present invention, the brightness of the subject contained in the fluoroscopic image is also regarded upon determination of the radiography condition. This achieves obtaining the suitable radiography condition even when obtaining the animated image stops before the radiation has appropriate intensity during obtaining the animated image. Accordingly, the apparatus in the embodiment of the present invention allows obtaining a clear static image with appropriate exposure.

BRIEF DESCRIPTION OF DRAWINGS

FIGS. 2 to 4 are schematic views each illustrating the X-ray apparatus according to the embodiment.

FIG. 8 is a function block diagram illustrating operation of the apparatus according to the embodiment.

DESCRIPTION OF EMBODIMENTS

The following describes one embodiment of the present invention. X-rays in embodiments correspond to the radiation in the present invention. An FPD is an abbreviation for a flat panel detector.

Embodiment 1

<Overall Construction of X-Ray Apparatus>

Figure 1:
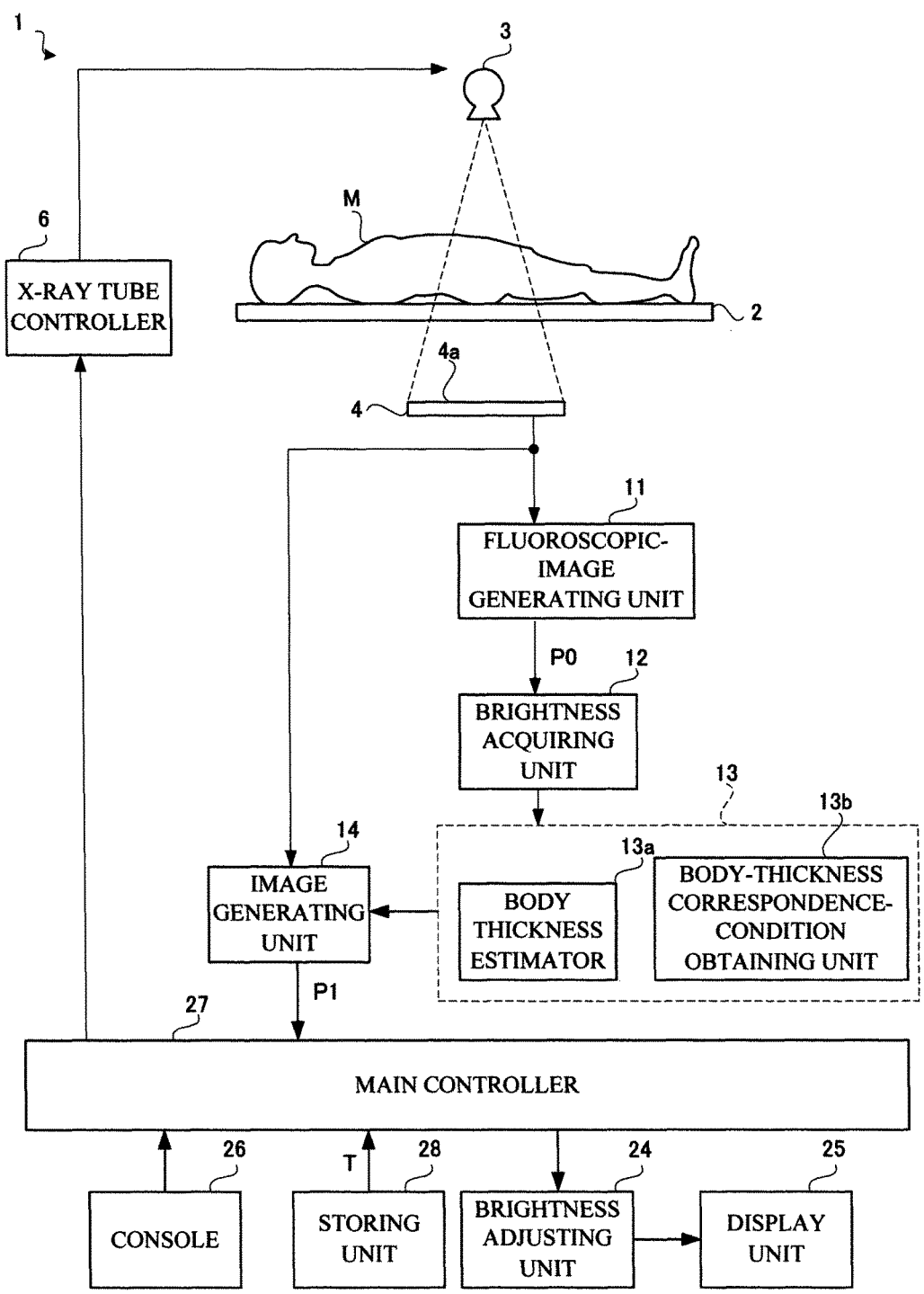
FIG. 1 is a function block diagram illustrating an X-ray apparatus according to one embodiment of the present invention.

Firstly, description will be given of an X-ray apparatus 1 according to Embodiment 1. As illustrated in FIG. 1, an X-ray apparatus 1 includes a top board 2 configured to support a subject M placed thereon in a supine position, an X-ray tube 3 above the top board 2 (at a first face side) for emitting X-rays, and an FPD 4 below the top board 2 (at a second face side) for detecting X-rays. The FPD 4 is rectangular having four sides along either a body axis direction or a body side direction of the subject M. The X-ray tube 3 emits X-rays in a quadrangular pyramid shape to the FPD 4. An entire surface of the FPD 4 receives X-rays. The FPD 4 has a detecting surface 4a configured to detect X-rays, the detecting surface having X-ray detecting elements arranged two-dimensionally in the body axis direction and the body side direction. The X-ray tube 3 corresponds to the radiation source in the present invention. The FPD 4 corresponds to the radiation detecting device in the present invention.

The X-ray apparatus 1 in the embodiment takes a fluoroscopic image P0 in the form of an animated image, and thereafter takes an image P1. The fluoroscopic image P0 is obtained for determining a position of the subject M in advance prior to taking the image P1. The image P1 is obtained for conducting diagnosis to the subject M and recording lesion or treatment of the subject M.

An X-ray tube controller 6 is provided for controlling the X-ray tube 3. The X-ray tube controller 6 controls the X-ray tube 3 by transmitting various control parameters, such as a tube current, a tube voltage, and a pulse width, to the X-ray tube 3. The X-ray tube controller 6 corresponds to the radiation source controller in the present invention.

A fluoroscopic-image generating unit 11 generates the fluoroscopic image P0. That is, the fluoroscopic-image generating unit 11 generates an animated image of the fluoroscopic image P0 in accordance with detection signals outputted from the FPD 4. A brightness adjusting unit 24 controls brightness of the fluoroscopic image P0 in the form of the animated image, and a display unit 25 displays the brightness in real time. At this time, the X-ray tube 3 continuously irradiates the subject M with weak X-rays over time while the fluoroscopic image P0 is obtained. Here, the fluoroscopic-image generating unit 11 corresponds to the fluoroscopic-image generating device in the present invention.

The fluoroscopic image P0 is also sent to a brightness acquiring unit 12. The brightness acquiring unit 12 acquires the brightness of the subject M in the fluoroscopic image P0 appearing in the animated image. At this time, the brightness acquiring unit 12 extracts a photometric area from the fluoroscopic image P0 to eliminate a black peak and a white peak, and thereafter averages pixel values in the photometric area. In this manner, the brightness acquiring unit 12 determines the brightness. For instance, the brightness of the fluoroscopic image P0 higher than a reference value represents that the body thickness of the subject M is small and thus X-rays readily transmit through the subject M. On the other hand, the brightness of the fluoroscopic image P0 lower than the reference value represents that the body thickness of the subject M is large and thus X-rays have difficulty in transmitting through the subject M. Taking into consideration that the fluoroscopic image P0 is an animated image, the brightness acquiring unit 12 acquires current brightness in real time. Here, the brightness acquiring unit 12 corresponds to the brightness acquiring device in the present invention.

The brightness acquiring unit 12 sends the brightness in real time to a radiography condition obtaining unit 13. The radiography condition obtaining unit 13 also receives the control condition of the X-ray tube 3 from the X-ray tube controller 6 in real time. The radiography condition obtaining unit 13 obtains the control condition (radiography condition) of the X-ray tube 3 in accordance with the brightness of the subject M in the fluoroscopic image P0 and the control condition of the X-ray tube 3 upon obtaining the fluoroscopic image. The radiography condition is obtained upon subsequent taking of the static image or the animated image. Here, the radiography condition obtaining unit 13 corresponds to the radiography condition obtaining device in the present invention.

The following describes a concrete construction of the radiography condition obtaining unit 13. The radiography condition obtaining unit 13 includes a body thickness estimator 13a and a body-thickness correspondence-condition obtaining unit 13b. The body thickness estimator 13a estimates a body thickness of the subject M in accordance with the control condition of the X-ray tube 3 upon obtaining the fluoroscopic image and the brightness of the subject M in the fluoroscopic image P0. The body-thickness correspondence-condition obtaining unit 13b obtains a control condition (radiography condition) of the X-ray tube 3 corresponding to the estimated body thickness. In such a manner, the radiography condition obtaining unit 13 outputs the control condition (radiography condition) of the X-ray tube 3 upon taking the image in accordance with input of the control condition of the X-ray tube 3 and the brightness of the subject M in the fluoroscopic image P0. The radiography condition is outputted in accordance with the final control condition of the X-ray tube 3 and the final brightness of the fluoroscopic image P0 during the fluoroscopy. Here, the body thickness estimator 13a corresponds to the body thickness estimating device in the present invention. The body-thickness correspondence-condition obtaining unit 13b corresponds to the body-thickness correspondence-condition obtaining device in the present invention.

The following describes operation of the body thickness estimator 13a. The body thickness estimator 13a reads out a table T1 from a storing unit 28, the table T1 having a relationship between the control condition of the X-ray tube 3 upon obtaining the fluoroscopic image and the body thickness of the subject M. Thereafter, the body thickness estimator 13a acquires the body thickness of the subject M, corresponding to the final control condition during the fluoroscopy, in accordance with the table T1. As illustrated in FIG. 2, the table T1 has a relationship between the control condition of the X-ray tube 3 during fluoroscopy and the body thickness of the subject M. The control condition listed on the left of the table T1 is a control condition suitable for fluoroscopy of the subject M having the body thickness listed on the right of the table T1. Here, the body thickness of the subject M obtained at this time is to be referred to as a standard body thickness ST. The control condition of the X-ray tube 3 in the table T1 corresponds to a tube current and a tube voltage of the X-ray tube 3, for example. Here, the storing unit 28 corresponds to the storing device in the present invention.

The body thickness estimator 13a estimates an actual body thickness of the subject M by estimating how the actual body thickness differs from the standard body thickness ST in accordance with the brightness of the fluoroscopic image P0. Specifically, the body thickness estimator 13a firstly subtracts the final brightness of the subject M appearing in the fluoroscopic image P0 during fluoroscopy from the standard brightness, thereby acquiring a brightness difference D. Here, the standard brightness is appropriate to the fluoroscopy of the subject M. When the X-ray tube 3 is controlled under the condition listed on the left of the table T1 and the fluoroscopy is performed to the subject M having a body thickness listed in the right of the table T1, the acquired brightness of the fluoroscopic image P0 is the standard brightness.

The body thickness estimator 13a acquires a correction value T_comp for the body thickness in accordance with the acquired brightness difference D. The body thickness estimator 13a reads out a table T2 having a relationship between the correction value and the brightness difference D from the storing unit 28, thereby obtaining the correction value T_comp corresponding to the brightness difference D (as for the table T2, see FIG. 3). The correction value T_comp represents a difference of the actual body thickness relative to the standard body thickness ST. For instance, when the brightness difference D has a positive value, the fluoroscopic image P0 has the actual brightness lower than the standard value and contains the subject M appearing therein darkly. Consequently, the actual body thickness of the subject M is larger than the standard body thickness ST (i.e., the correction value T_comp is positive). On the other hand, when the brightness difference D has a negative value, the fluoroscopic image P0 has the actual brightness larger than the standard value and contains the subject M appearing therein brightly. Consequently, the actual body thickness of the subject M is smaller than the standard body thickness ST (i.e., the correction value T_comp is negative).

The body thickness estimator 13a adds the correction value T_comp to the standard body thickness ST to estimate the actual body thickness of the subject M. The body thickness estimator 13a may estimate the actual body thickness in accordance with the brightness subjected to log conversion processing.

The body thickness estimator 13a sends the actual body thickness to the body-thickness correspondence-condition obtaining unit 13b. The body-thickness correspondence-condition obtaining unit 13b reads out a table T3 illustrated in FIG. 4 from the storing unit 28, thereby obtaining a radiography condition corresponding to the body thickness estimated with the body thickness estimator 13a. Here, the table T3 has a relationship between the body thickness and the radiography condition. The radiography condition at this time is a control condition of the X-ray tube 3 upon taking the image P1 for diagnosis of the subject M. The body-thickness correspondence-condition obtaining unit 13b sends the obtained radiography condition to the X-ray tube controller 6. The radiography condition is used for taking the image P1.

The brightness acquired with the brightness acquiring unit 12 is sent not only to the radiography condition obtaining unit 13 but also to the X-ray tube controller 6 in real time. The following describes control of the X-ray tube 3 by the X-ray tube controller 6 in accordance with the brightness. When receiving the brightness from the brightness acquiring unit 12, the X-ray tube controller 6 controls the X-ray tube 3 so as the brightness of the fluoroscopic image P0 to be close to the standard brightness. The FPD 4 detects X-rays emitted under the changed control as above. The brightness of the fluoroscopic image P0 at this time is sent to the X-ray tube controller 6. Then the X-ray tube controller 6 again controls the X-ray tube 3 so as the brightness of the fluoroscopic image P0 to be close to the standard brightness. As noted above, the X-ray tube controller 6 performs feedback control to the X-ray tube 3 in accordance with actual measurement of the brightness of the fluoroscopic image P0. Here, the standard brightness is a brightness with which the fluoroscopic image P0 is suitably visible.

An image generating unit 14 generates the image P1 (static image) in accordance with the detection signals that the FPD 4 outputs during radiography. Specifically, the image generating unit 14 generates the image P1 from the detection signals of the FPD 4 that detects the X-rays from the X-ray tube 3 in accordance with the radiography condition obtained with the radiography condition obtaining unit 13. The image generating unit 14 corresponds to the image generating device in the present invention.

The display unit 25 is provided for displaying the fluoroscopic image P0 and the image P1. The brightness adjusting unit 24 controls the brightness of the fluoroscopic image P0 in the form of the animated image in real time, thereby complementing difficulty in visibility of the image due to an insufficient or excessive dose of X-rays during fluoroscopy.

A console 26 (see FIG. 1) is provided for inputting operator's instructions such as start of emitting X-rays. The operator can change the X-ray irradiation condition upon fluoroscopy via the console 26. A main controller 27 is also provided for controlling each controller en bloc. The main controller 27 has a CPU, and executes the X-ray tube controller 6 and each unit by executing various programs. The above units may be divided into arithmetic units that perform their functions. The storing unit 28 stores the tables T1, T2 and T3. The table T1 represents a relationship between the control condition of the X-ray tube 3 upon obtaining the fluoroscopic image (during fluoroscopy) and the standard body thickness ST. The table T2 represents a relationship between the brightness difference D and the correction value. The table T3 represents a relationship between the body thickness and the radiography condition. Here, the console 26 corresponds to the input device in the present invention.

Effect of Embodiment 1

Figure 5:
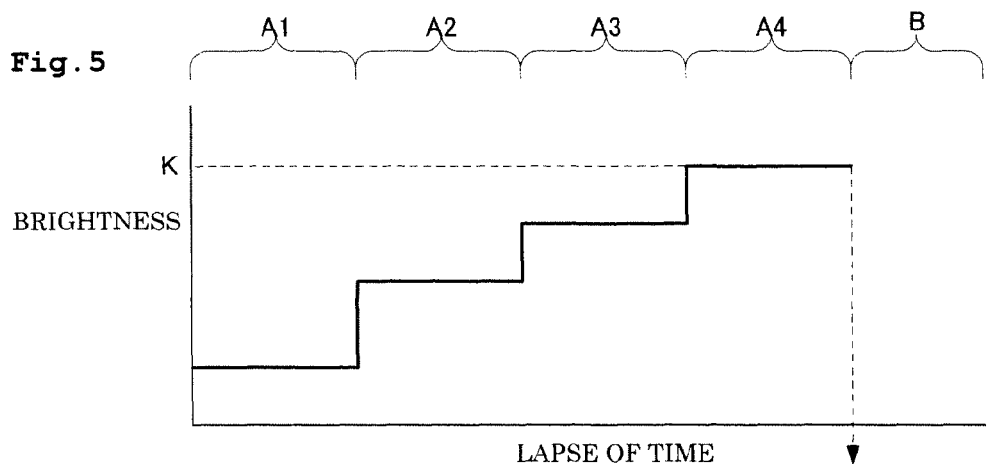
FIGS. 5 to 7 are schematic views each illustrating an effect of the embodiment.

The following describes an effect of Embodiment 1. FIG. 5 illustrates over-time variation in brightness of the fluoroscopic image representing X-ray radiography with a conventional X-ray apparatus. Here, a longitudinal axis indicates brightness of the fluoroscopic image P0, whereas a horizontal axis indicates a lapse of time. FIG. 5 illustrates time periods denoted by A1 to A4, the time periods corresponding to time periods during which obtaining an animated image of the fluoroscopic image P0 is completed and the operator aligns the subject M. FIG. 5 illustrates a time period denoted by B. The time period corresponds to a time period during which obtaining the animated image of the fluoroscopic image P0 is completed and the image P1 is taken.

FIG. 5 illustrates standard brightness denoted by a numeral K. Here, the standard brightness corresponds to brightness with which the fluoroscopic image P0 is suitably visible. Consequently, at the beginning of fluoroscopy in FIG. 5, the fluoroscopic image P0 has brightness much lower than the standard brightness K.

From this condition, the X-ray tube controller 6 performs feedback control to the X-ray tube 3, whereby the brightness of the fluoroscopic image P0 is close to the standard brightness K. Specifically, the X-ray tube controller 6 causes the brightness of the fluoroscopic image P0 be close to the standard brightness K by stepwise changing the control condition of the X-ray tube 3 in the time period A1 for three times. Accordingly, the fluoroscopic image P0 becomes brighter every time the X-ray tube controller 6 changes the control condition. This leads to enhanced visibility of the fluoroscopic image P0.

FIG. 5 illustrates the time period A4 during which the feedback control by the X-ray tube controller 6 causes the brightness of the fluoroscopic image P0 to reach the standard brightness K. At this time, the operator completes alignment of the subject M while visually recognizing the fluoroscopic image P0 having sufficient clearness for aligning the subject M. The fluoroscopy in the time periods A1 to A4 is completed to stop emitting X-rays.

The fluoroscopy is performed for the purpose of determining the radiography condition in addition to the purpose of aligning of the subject. Specifically, when the fluoroscopy in the time periods A1 to A4 is completed, the radiography condition for taking the image P1 is obtained in accordance with the final X-ray tube control condition during the fluoroscopy. Here, the radiography condition at this time is expressed by a radiography condition 4. The X-ray tube 3 is controlled based on the obtained radiography condition 4, and the image P1 is taken. The image P1 is taken in a time period B in FIG. 5. This corresponds to a conventional imaging mode. Here, the radiography condition is determined under an assumption that the brightness of the fluoroscopic image P0 has already reached the standard brightness K.

However, the recent apparatus includes a brightness adjusting unit 24 or the like. This controls the brightness of the fluoroscopic image P0 to enhance visibility thereof, and then the display unit 25 displays the fluoroscopic image P0. Accordingly, the feedback control of the X-ray tube 3 causes the display unit 25 to display the clear fluoroscopic image P0 having the controlled brightness before the brightness of the fluoroscopic image P0 reaches the standard brightness K. As a result, the operator may complete the alignment of the subject M before the time period A4 in FIG. 5.

Figure 6:
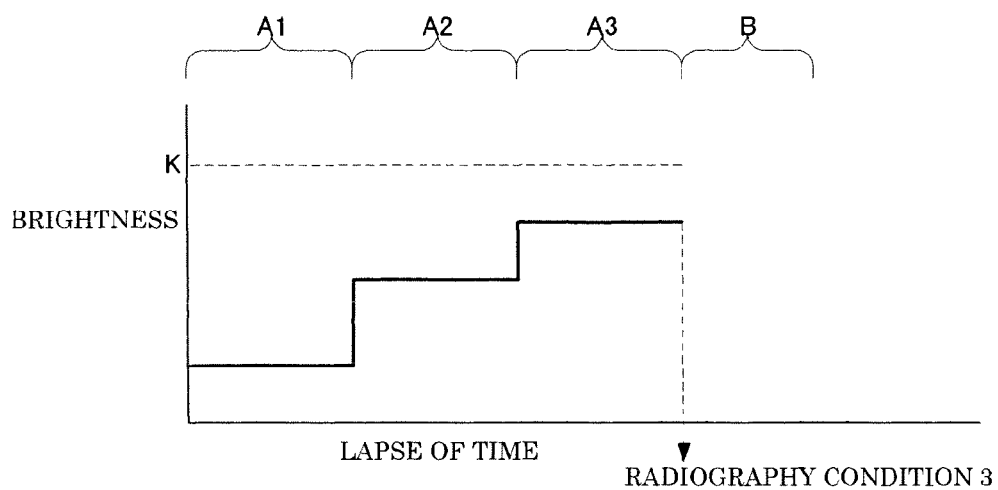

The operator completes obtaining the fluoroscopic image P0 immediately after the alignment of the subject M for avoiding undesirable exposure to the subject M. Then, as illustrated in FIG. 6, the feedback control stops the fluoroscopy before the fluoroscopic image P0 reaches the standard brightness K. The radiography condition for taking the image P1 is determined in accordance with the final X-ray tube control condition in the fluoroscopy. Consequently, the radiography condition obtained in FIG. 6 is a radiography condition 3 that is different from the radiography condition 4 obtained in FIG. 5. Accordingly, in FIG. 6, the image P1 is subsequently taken in accordance with the radiography condition 3.

The image P1 is taken under the radiography condition 3 with an insufficient dose of X-rays, and thus is not clear. The radiography condition 3 is suitable when the brightness of the fluoroscopic image P0 is the standard brightness K in the time period A3, and unsuitable when the brightness of the fluoroscopic image P0 is out of the standard brightness K as illustrated in FIG. 6. It is conceivable that such a phenomenon occurs because the fluoroscopy is cut off early to cause the apparatus to misidentify the body thickness of the subject, failing to obtain a suitable radiography condition.

Figure 7:
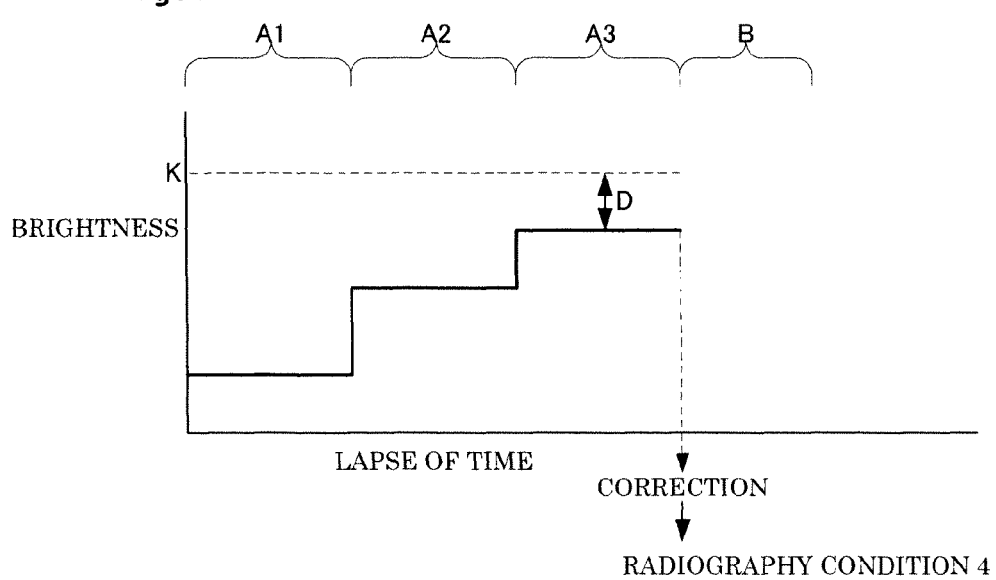

FIG. 7 illustrates a configuration of Embodiment 1. In the configuration of Embodiment 1, a difference (brightness difference D) between the brightness of the fluoroscopic image P0 at the time of completing the fluoroscopy and the standard brightness K is obtained, and correction is made in accordance with the brightness difference D, whereby a radiography condition is obtained. Consequently, Embodiment 1 allows obtaining the suitable radiography condition 4 although the fluoroscopy is completed in the time period A3, and the radiography condition 4 is used for taking the image P1 in the subsequent stage. This allows obtaining the image P1 through control of the X-ray tube 3 under the suitable radiography condition although the brightness of the fluoroscopic image P0 does not reach the standard brightness K by the feedback control.

<Operation of X-Ray Apparatus>

The following describes operation of the X-ray apparatus in Embodiment 1. The subject M is firstly placed on the top board 2, as illustrated in FIG. 8, for radiography of the subject M with the X-ray apparatus 1 (a subject placing step S1). Thereafter, an operator issues a command via the console 26 to the X-ray apparatus 1 to start fluoroscopy. Accordingly, the X-ray tube 3 starts emitting weak X-rays, and obtaining the fluoroscopic image P0 in the form of an animated image starts (a fluoroscopy step S2). The display unit 25 displays the fluoroscopic image P0 in real time.

The operator aligns the subject M on the top board while visibly recognizing the fluoroscopic image P0. The X-ray tube 3 is subjected to the feedback control during this, whereby intensity of X-rays is updated to be higher. Upon completion of alignment of the subject M, the operator issues a command via the console 26 to the X-ray apparatus 1 to complete the fluoroscopy, whereby emission of X-rays stops.

Thereafter, the radiography condition obtaining unit 13 obtains a suitable radiography condition in accordance with the final X-ray tube control condition and the final brightness of the fluoroscopic image P0 during fluoroscopy (a radiography condition obtaining step S3). Here, Embodiment 1 achieves obtaining a suitable radiography condition even when the X-ray tube control condition is unsuitable for fluoroscopy. This has already been described. Then, when the operator issues a command via the console 26 to the X-ray apparatus 1 to start radiography, the X-ray tube 3 emits strong X-rays only once in accordance with the radiography condition obtained with the radiography condition obtaining unit 13, whereby an image P1 is taken (a radiography step S4). Then the display unit 25 displays the image P1 to complete a series of operation. In the radiography step S4, an animated image may be taken instead of the image P1. At this time, the image generating unit 14 generates the animated image instead of the image P1.

As noted above, the apparatus in the embodiment of the present invention obtains the animated image of the fluoroscopic image P0, and thereafter completes fluoroscopy temporarily for taking the animated image or the static image for diagnosis. The apparatus in the embodiment of the present invention determines the control condition (radiography condition) of the X-ray tube 3 for taking the static image in accordance with the control condition of the X-ray tube 3 upon obtaining the fluoroscopic image P0. On the other hand, the radiography condition is determined under this state regardless of a body thickness of the subject M. Consequently, the radiography condition is not always suitable. Accordingly, in the embodiment of the present invention, the brightness of the subject M appearing in the fluoroscopic image is also regarded upon determination of the radiography condition. Here, the brightness of the subject M varies depending on the body thickness of the subject M. Consequently, correction of the radiography condition depending on the brightness of the subject achieves a suitable radiography condition depending on the body thickness of the subject M. As a result, the apparatus in the embodiment of the present invention allows obtaining the clear static image or the animated image with appropriate exposure.

Moreover, when the present invention is applied to a configuration of performing feedback control to the X-ray tube 3 upon obtaining the fluoroscopic image P0, a clear static image or an animated image with appropriate exposure is obtainable although taking the fluoroscopic image P0 stops before the control condition of the X-ray tube 3 becomes suitable upon obtaining the fluoroscopic image P0 through the feedback control.

The present invention is applicable to the apparatus that allows variations of the radiation irradiation condition upon obtaining the fluoroscopic image. Although the operator misjudges visually when the radiation irradiation condition is changed to be suitable upon obtaining the fluoroscopic image, a function of the apparatus in the present invention naturally achieves the suitable radiography condition.

Moreover, in the embodiment of the present invention, the radiography condition is obtained by temporarily estimating the body thickness of the subject M. This achieves rapid adaptation to variations in configuration of the apparatus, and additionally ensures to obtain the radiography condition.

Moreover, obtaining the radiography condition in accordance with information stored in the storing device 28 ensures to obtain the radiography condition rapidly.

The present invention is not limited to the embodiment mentioned above, but may be modified as under.

(1) In the above embodiment, the body thickness estimator 13a and the body-thickness correspondence-condition obtaining unit 13b operate in accordance with various tables stored in the storing unit 28. However, the present invention is not limited to this. Instead of the various tables, functions may be adopted.

(2) The foregoing embodiment discusses an apparatus for medical use. The present invention is also applicable to an apparatus for industrial use or for the nuclear field.

(3) X-rays described in the foregoing embodiment are an example of radiation in the present invention. Therefore, the present invention is also applicable to radiation other than X-rays.

INDUSTRIAL APPLICABILITY

The present invention is suitable for a medical radiographic apparatus.

REFERENCE SIGN LIST

3 X-ray tube (radiation source)
6 X-ray tube controller (radiation source controller)
4 FPD (detecting device)
11 fluoroscopic-image generating unit (fluoroscopic-image generating device)
12 brightness acquiring unit (brightness acquiring device)
13 radiography condition obtaining unit (radiography condition obtaining device)
13a body thickness estimator (body thickness estimating device)
13b body-thickness correspondence-condition obtaining unit (body-thickness correspondence-condition obtaining device)
14 image generating unit (image generating device)
26 console (input device)
28 storing unit (storing device)

The invention claimed is:
1. A radiographic apparatus, comprising:
a radiation source configured to emit radiation;
a radiation source controller configured to control the radiation source;
a detecting device configured to detect radiation through a subject to output a detection signal;

a fluoroscopic-image generating device configured to generate an animated image of a fluoroscopic image of the subject in accordance with the detection signal;

a brightness acquiring device configured to acquire brightness of the subject contained in the fluoroscopic image;

a radiography condition obtaining device configured to obtain a radiography condition in accordance with the brightness of the subject in the fluoroscopic image before an irradiation condition for taking the fluoroscopy image becomes suitable and a control condition of the radiation source as a condition for controlling a tube current and a tube voltage, the radiography condition being a condition for a static image or an animation image subsequent to obtaining the fluoroscopic-image; and an image generating device configured to generate the static image or the animated image in accordance with the radiography condition.

2. The radiographic apparatus according to claim 1, wherein
the radiation source controller performs feedback control to the radiation source upon obtaining the fluoroscopic image in accordance with the brightness of the subject in the fluoroscopic image obtained with the brightness acquiring device.

3. The radiographic apparatus according to claim 1, further comprising:
an input device configured to input variations in the irradiation condition by an operator upon obtaining the fluoroscopic image.

4. The radiographic apparatus according to claim 1, wherein
the radiography condition obtaining device includes:
a body thickness estimating device configured to estimate a body thickness of the subject in accordance with the control condition of the radiation source and the brightness of the subject in the fluoroscopic image; and
a body-thickness correspondence-condition obtaining device configured to obtain the control condition of the radiation source corresponding to the estimated body thickness.

5. The radiographic apparatus according to claim 4, further comprising:
a storing device configured to store a correspondence between the control condition of the radiation source upon obtaining the fluoroscopic image and the body thickness and a correspondence between the body thickness and the radiography condition.

* * * * *